US007256202B2

United States Patent
Halow

(10) Patent No.: US 7,256,202 B2
(45) Date of Patent: Aug. 14, 2007

(54) COMPOSITION AND METHOD FOR TREATMENT OF HEPATIC ENCEPHALOPATHY

(76) Inventor: George M. Halow, 4305 Okoefe Dr., El Paso, TX (US) 79902

( * ) Notice: Subject to any disclaimer, the term of this patent is extended or adjusted under 35 U.S.C. 154(b) by 193 days.

(21) Appl. No.: 10/748,185

(22) Filed: Dec. 31, 2003

(65) Prior Publication Data

US 2005/0142099 A1    Jun. 30, 2005

(51) Int. Cl.
*A61K 31/4709*    (2006.01)
(52) U.S. Cl. ..................................................... 514/312
(58) Field of Classification Search ............ 424/78.38, 424/601, 692, 697, 738; 514/53, 57, 312
See application file for complete search history.

(56) References Cited

U.S. PATENT DOCUMENTS

| | | | | |
|---|---|---|---|---|
| 3,505,309 A | * | 4/1970 | Carubelli ..................... | 536/125 |
| 3,716,408 A | * | 2/1973 | Nagasawa et al. .......... | 127/46.1 |
| 4,057,655 A | * | 11/1977 | Okada et al. ................. | 426/583 |
| 4,100,293 A | * | 7/1978 | Walser ........................ | 514/562 |
| 4,147,773 A | * | 4/1979 | Ogasa ......................... | 424/93.4 |
| 4,996,236 A |   | 2/1991 | Nakamura et al. | |
| 5,326,405 A | * | 7/1994 | Pluim et al. .................. | 127/42 |
| 5,415,695 A | * | 5/1995 | Weterings et al. ............ | 127/58 |
| 5,571,783 A |   | 11/1996 | Montagne et al. | |
| 5,688,521 A | * | 11/1997 | Bolder et al. ................ | 424/439 |
| 6,444,198 B1 | * | 9/2002 | Daggy et al. ............ | 424/78.01 |
| 6,488,969 B1 | * | 12/2002 | Tsutsumi et al. ........... | 424/776 |
| 6,645,481 B1 | * | 11/2003 | Cleveland et al. ....... | 424/78.01 |
| 2005/0152989 A1 | * | 7/2005 | Pelham et al. ................ | 424/60 |

FOREIGN PATENT DOCUMENTS

EP    1230918 A2 *    8/2002

OTHER PUBLICATIONS

Mosby's (Mosby's GenRx: The complete reference for generic and brand drugs, Eighth Edition, 1998, Mosby—Year Book Inc., Publishers, St. Louis, p. II-1169 & II-1770).*
Roblin, et al. ("Use of polyethylene glycol 4000 in hepatic encephalopathy related to digestive hemorrages," Gastroenterol Clin Biol 1994 18(12): 1146)—Full article from French.*
"Duphalac Dry" product information brochure, www.intekom.com, publication date May 27, 1994.*
Bond et al., Journal of Laboratory and Clinical Medicine, 1975, 85(4), pp. 546-555.*
"Ammonia", www.labtestonline.org, 2004.*
"Encephalopathy, Hepatic", www.emedicine, 2006.*

* cited by examiner

*Primary Examiner*—Brian Kwon
(74) *Attorney, Agent, or Firm*—Hoffman, Wasson & Gitler; Jean A. Buttmi

(57) ABSTRACT

The inventions provide an improved treatment for hepatic encephalopathy characterized by hyperammonemia and/or constipation, comprising the oral administration of polyethylene glycol (PEG) in amounts sufficient to reduce plasma levels of ammonia and/or to alleviate constipation. Preferably, the PEG is administered in combination with lactulose, which provides a palatable composition for the treatment of HE with excellent therapeutic benefits and reduced side effects as compared to lactulose alone.

24 Claims, No Drawings

COMPOSITION AND METHOD FOR TREATMENT OF HEPATIC ENCEPHALOPATHY

BACKGROUND OF THE INVENTION

1. Field of Art

Hepatic encephalopathy (HE) is a syndrome associated with liver dysfunction, characterized by a decline in mental function and neurological abnormalities. Distinctive clinical signs include personality changes and intellectual impairment, and neuromuscular anomalies such as asterixis (flapping tremor) and alterations in gait.

The syndrome typically manifests in patients with an extensive collateral blood vessel system (extrahepatic portal shunts) which diverts portal venous blood away from the liver into the systemic circulation. Thus, toxic metabolites absorbed into the bloodstream from the intestines may largely bypass the liver and enter the general circulatory system without being detoxified. Among other ramifications, such toxins can cause metabolic aberrations in the central nervous system (CNS) which lead to increased permeability of the blood-brain barrier and increased transport of toxic substances across this barrier into the brain. In addition to promoting permeability of the neuronal membrane, high plasma levels of certain neurotoxins are thought to contribute to changes in energy metabolism and nerve processes in the brain. Neurotoxins which have been implicated in the pathogenesis of hepatic encephalopathy include false neurotransmitters, mercaptans, γ-amino butyric acid, and ammonia.

Ammonia is normally produced in the gastrointestinal tract by bacterial degradation of peptides and other nitrogen-containing compounds, and then detoxified in the liver by conversion to urea and glutamine. If the liver is sufficiently diseased, or bypassed as when portal shunts are present, plasma levels of ammonia may increase to toxic levels, affecting, for example, the transport of amines, water, and electrolytes across the neuronal membrane. While the role that ammonia plays in the pathogenesis of hepatic encephalopathy is not entirely clear, reduction of plasma levels of ammonia has been clinically observed to improve HE in many cases, and evaluation of ammonia blood levels for hyperammonemia is widely routine in suspected cases.

2. Discussion of Related Art

A common treatment of hyperammonemia in hepatic encephalopathy is the oral administration of lactulose, a disaccharide of fructose and galactose. Lactulose is not metabolized by mammals and reaches the large intestine substantially intact, where it is digested by resident microorganisms to produce organic acids (lactic, formic, acetic) and $CO_2$. High local concentrations of lactulose draw free ammonia in solution from the bloodstream into the bowel where it reacts with these acids to form their ammonium salts which are then excreted.

In addition to ammonia detoxification in HE, lactulose additionally functions as an osmotic laxative or stool softener by increasing gut solute concentrations and drawing water into the large intestine. As constipation as well as hyperammonemia is a common condition in HE, lactulose is a significant therapy for patients. However, it is very difficult to obtain compliance from patients for several reasons, mainly that current lactulose formulations have a very bad taste, and that at the required dosages they frequently cause bloating and nausea to the point of significant discomfort.

SUMMARY OF THE DISCLOSURE

The inventions provide an improved treatment for hepatic encephalopathy characterized by hyperammonemia and/or constipation, comprising the oral administration of polyethylene glycol (PEG) in amounts sufficient to reduce plasma levels of ammonia and/or to alleviate constipation. Preferably, the PEG is administered in combination with lactulose, which provides a palatable composition for the treatment of HE with excellent therapeutic benefits and reduced side effects as compared to lactulose alone.

DETAILED DESCRIPTION OF THE INVENTIONS

As described at length in U.S. Pat. No. 5,710,183 issued 20 Jan. 1998 to the present inventor, PEG has been used as an osmotic bowel cleanser or laxative which draws water into the bowel, thereby increasing bowel motility and softening the stool. The present inventions are predicated on the discovery that the osmotic effects of PEG are useful not only for softening the stool and/or increasing bowel motility of constipated HE patients, but also for inhibiting production of ammonia in the bowel of patients at risk of hyperammonemia by accelerating the passage of proteins and other nitrogenous metabolites through the gastrointestinal tract. By reducing the residence time of ingested food in the digestive system, catabolism of metabolites yielding ammonia byproduct is minimized. The residence time can be managed by adjusting the PEG dosage for the desired results; if, for example, a dietary overload of protein has precipitated or exacerbated an occurrence of HE, higher and/or more frequent dosages of PEG which will induce at least moderate diarrhea to minimize protein digestion and the consequent production of ammonia, may be desirable. In severe cases, one may want to use amounts of PEG suitable for bowel cleansing, for example as set forth in U.S. Pat. No. 5,710,183, incorporated herein by reference.

In a preferred embodiment, the invention comprises a composition of PEG and lactulose powder for the treatment of constipation and/or hyperammonemia in HE or other needy patients. This composition combines the osmotic properties of lactulose and PEG for laxative/stool softening benefits; additionally, these same osmotic properties increase the fluid volume in the gut by drawing in liquid containing excess free ammonia, which facilitates conversion of this toxin to harmless ammonium salts in the presence of endogenous bacteria and lactulose as detailed supra. Thus, lactulose both enhances the osmotic properties of the PEG and mediates detoxification of ammonia entering the intestine by osmosis. Further, the gas and cramping which frequently occurs with the use of lactulose alone for treating HE is significantly reduced, owing in part to the significantly lower dosage (½ to ⅓ the standard dose) used herein. Importantly, compositions of the invention containing both lactulose and PEG are effective in low volume, low frequency dosages and are also surprisingly palatable so that patients are far more compliant with their treatment regimens and results are significantly improved.

Polyethylene glycols useful in the composition of the invention broadly comprise any food-grade or pharmaceutical-grade PEG. Currently preferred for convenience of use in preparing and using the composition of the invention are polymers having molecular weights above about 900 which are solid at room temperature and soluble in or miscible with water. Polymers having average molecular weights between about 3000 and 8000 are exemplary; PEG 4000, which is nearly odorless and tasteless and widely available in USP grade, or PEG 3350, are very suitable. These and other suitable PEG powders are commercially available, from, for example, Spectrum Chemical Mfg. Company, Gardena, Calif. A proprietary laxative, MiraLax® (Braintree Laboratories, Braintree, Mass.) is a useful source of PEG 3350 powder readily soluble in water. Non-powdered PEG should be comminuted to a particle size that is readily soluble/miscible in water before use. Lower molecular weight polymers such as PEG 400 which are liquid at room temperature may also be used in the practice of the invention, however, they are not generally expected to be as satisfactory as higher molecular weight PEGs. PEG compositions without added electrolytes such as found in Colyte® (Schwartz Pharma, Milwaukee) and other proprietary PEG-based bowel lavages, are preferred for their better taste.

Lactulose for the practice of the invention is readily available over-the-counter. A convenient and relatively tasteless formulation, often referred to in the trade as "lactulose powder for oral solution" can be obtained, for example, from Bertek Pharmaceuticals, Sugarland, Tex. as Kristalose® in 10 and 20 gm packets. The lactulose syrups commonly sold as laxatives such as Cephulac®, Chronulac®, Cholac®, and Enulose® are not preferred in the practice of the present inventions as several contain undesirable additives and many patients object to their taste. However, such syrups can be substituted for lactulose powder by using sufficient syrup to provide the desired dosage of lactulose; typically, the named syrups contain about 10 gm lactulose in 15 ml of syrup.

PEG and lactulose are each prepared as described above, conveniently as powders, for ready solubility/dispersability in water or other aqueous liquid such as juice to provide a palatable drink for liquid administration. If a PEG/lactulose composition is desired, the powders are then combined to form a dry composition and, for use, dissolved in the selected liquid. The PEG and lactulose components are typically combined in proportions of from about 0.15 to 3.5 parts by weight PEG to 1 part by weight lactulose; in many cases, a range of from about 0.5 to 2 or 0.5 to 3 parts by weight of PEG to 1 part by weight lactulose will be effective. If the PEG to lactulose ratio is too low, the side effects of the lactulose will become pronounced and compliance will drop off; if the PEG to lactulose ratio is too high, the volume of composition which must be ingested to obtain the benefits of the lactulose component may be undesirably high and the excess of PEG may exacerbate or precipitate undesirable side effects. Individual dosages will usually range from about 5 to 35 gm PEG and from about 10 to 30 gm lactulose powder (or more if it is indicated and can be tolerated). In mild-to-moderate or moderately severe cases of HE from about 10 to 20 gm PEG to about 10 to 20 gm lactulose is recommended as a starting dosage. In a particular example, about 10 gm powdered lactulose such as Kristalose® is admixed with about 17 gm powdered PEG 3350 (Spectrum Chemical Mfg. Company, Gardenia, Calif.) to provide a dry lactulose/dry PEG composition according to the invention comprising 1.7 parts by weight PEG to 1 part by weight lactulose, to be taken diluted with water or other water-based liquid to taste.

For use, the dry lactulose/dry PEG composition, with or without optional conventional additives such as electrolytes coloring matter, or flavorings, is dispersed/dissolved in sufficient water or other aqueous medium to formulate a relatively smooth, palatable drink. Single dosages of dry composition containing from about 5 to 35 gm of PEG, for example, about 17 gm, admixed with about 10 to 30 gm lactulose, for example about 10 gm, are conveniently dispersed/dissolved in from about 6 to 10 fl. oz., conveniently about 8 fl. oz., of water or other palatable water-based liquid such as juice, to provide a low-volume drink for oral administration. About two tablespoons of a dry lactulose/PEG composition according to the invention dissolved in about 8 fl. oz. of water and administered from about 1 to 3 times a day, usually 2 times a day, will generally provide satisfactory results. The volume of water or other liquid in which the dry composition is dissolved/dispersed is not critical; in fact, two to three or more extra glasses of water or other liquid in conjunction with each drink may be generally beneficial. The dosages can be administered once or twice a day or more if indicated (e.g., tid or qid) until HE symptoms have abated. Results achieved include alleviation of constipation with bowel movements from 2-4 times per day and reduction of toxic plasma ammonia levels by about 25% to 50% or more to clinically-acceptable stable levels.

The product has a relatively rapid response time of from one to about two days. A maximum response can be expected in from one to two weeks, with the response continuing on this plateau with continued use of the product. The product is not habit forming, and can be administered as needed or on a continuing basis for many weeks, months, or years, usually without significant problem. Dosages can be increased or decreased, or PEG or lactulose concentration increased or decreased to modulate results according to medical necessity. For example, moderate to heavy diarrhea may be initially desirable if, for example, HE has been precipitated by excessive protein intake, to flush nitrogenous compounds from the bowel before they are degraded to ammonia: in this case, an increase in the number of dosages per day may be helpful as may be an increase in PEG concentration in the dosage formulation, or both. Conversely, if for example, constipation has been substantially alleviated but ammonia levels remain undesirably high, an increase in the lactulose concentration of the dosage formulation may be helpful. In some cases, such as severe HE requiring hospitalization, it may be desirable to administer the PEG dosage separately from the lactulose dosage, as by alternating the selected amount of lactulose with the selected amount of PEG two or more times daily.

In an alternate mode of practice according to the invention, powdered lactulose may be combined with liquid PEG (polyethylene glycol polymer which is liquid at room temperature) or dissolved powdered PEG. Proportions for a suitable liquid PEG/lactulose composition comprise, for example, about 10 to 20 gms powdered lactulose in 8-10 fl. oz. of PEG. If desired, the liquid PEG/lactulose composition may be further diluted with water for oral administration; for this application, PEG soluble in or miscible with water at room temperature is much preferred. Diluted or undiluted, the liquid or liquified PEG/lactulose composition is conveniently administered orally, in a regimen as described above for a diluted dry lactulose PEG composition. The liquid compositions of lactulose syrup and PEG powder mentioned above can be similarly prepared, admixing for example from about 15 to 30 ml syrup containing 10 g lactulose/15 ml of syrup with from about 10 to 20 gm powdered PEG; this composition may also be diluted as desired for oral administration as described above. If desired, a suitable wetting agent is added to any of the liquid lactulose/PEG compositions to promote dispersal/dissolving of the dry matter in the liquid to make a reasonably smooth and palatable drink.

As previously noted, PEG in either powdered or liquid form can be efficacious alone, particularly in milder cases of HE. In this mode of practicing the invention, individual dosages of PEG in amounts of from about 5 to 35 gm, especially from 10 to 20 gm, powder or from about 8-10 fl. oz. liquid are administered to HE patients whose plasma ammonia levels require reduction, in amounts sufficient to effect this reduction in the regimens described supra for PEG/lactulose compositions, e.g., 1 to 3 times daily.

In practice the inventions described herein can provided a good clinical response with substantial resolution of both cognitive and physical symptoms of HE such as confusion and asterixis. Importantly, the inventions permit HE patients in many cases to maintain themselves on a restricted protein diet (30-40 g protein daily), without significant recurrence of HE.

The following Examples are illustrative of making, using, and practicing the invention.

EXAMPLE

The patient is a 78 year old female with cryptogenic cirrhosis, a type of cirrhosis which has unknown etiology. She has had extensive workups for chronic anemia in one of the major California hospitals and was placed on neomycin, Lasix, iron sulfate, lactulose, and Prevacid; she also was on a restricted protein diet to reduce ammonia production. She had intermittent episodes of hepatic encephalopathy during her hospitalization. The patient's hemoglobin slowly drops and she requires transfusions periodically because of portal gastropathy. The patient's ammonia levels are high, for which she takes lactulose up to three to four times a day; she has three to four to five bowel movements per day. The patient has a difficult time taking lactulose because of the nausea, abdominal discomfort, and bloating sensation she gets with the drug and its unpleasant taste. Although the therapeutic range is three to four bowel movements per day, it is very difficult for her to get to that range because of these effects.

The patient has required several hospitalizations for lethargy, declines in hemoglobin, and hepatic encephalopathy. She has intermittent episodes of abdominal discomfort and mild irritation of various small bowel loops.

Laboratory data shows creatinine at 1.5, albumin at 2.6, total bilirubin at 1.17, and hemoglobin in the 9 to 10-range constantly declining and requiring transfusions periodically. The platelet count is in the range of 57,000. The lowest level of ammonia has been 30 micromoles/L and several levels have been 80 to 90 micromoles/L with the patient taking the lactulose.

The patient has had three hospitalizations for hepatic encephalopathy and anemia, mostly resulting from poor compliance. The patient's last hospitalization was July 22nd. Four months later, the patient presented us with hepatic encephalopathy and bedsores.

She was switched to 17 g MiraLax® (PEG 3350 powder) combined with 10 g of lactulose dissolved in water and given twice a day. The patient's ammonia level is now in the 70 to 75-range of micromoles/L and holding fairly steady on a maintenance dosage of this composition once per day.

The patient is now alert and oriented with no tremor or asterixis or any signs of hepatic encephalopathy. The patient is more compliant and accepts the taste and does not get the bloating and nausea and crampy sensations associated with lactulose. She has achieved clinical and therapeutic levels of ammonia levels, and is oriented to time and place, with no clinical signs of hepatic encephalopathy on physical examination.

What is claimed is:

1. A method for the treatment of a patient with hyperammonemia, comprising orally administering to the patient a pharmaceutical composition free of serum electrolytes and comprising from about 0.15 to 3.5 parts by weight polyethylene glycol (PEG) to about 1 part by weight lactulose, in an amount and frequency sufficient to reduce patient plasma ammonia to a clinically-acceptable level or to maintain this level, or both.

2. The method of claim 1, wherein the composition is a dry composition formulated as a liquid drink by admixture with a pharmaceutically-acceptable aqueous carrier.

3. The method of claim 1, wherein the composition comprises from about 0.5 to 3 parts by weight PEG to 1 part by weight lactulose.

4. The method of claim 2, wherein the composition is administered in single dosages each comprising about 5 to 35 gm of dry PEG dissolved in the aqueous carrier.

5. The method of claim 4, wherein each single dosage further comprises about 10 to 30 gm of dry lactulose dissolved in the aqueous carrier.

6. The method of claim 5, wherein each single dosage comprises about 10 to 20 gm PEG and about 10 to 20 gm lactulose dissolved in the aqueous carrier.

7. The method of claim 1, wherein the PEG is solid at room temperature.

8. The method of claim 4, wherein the composition is administered on a continuing basis in at least one single dosage per day.

9. The method of claim 5, wherein the composition is administered on a continuing basis in at least one single dosage per day.

10. The method of claim 6, wherein the composition is administered on a continuing basis in at least one single dosage per day.

11. The method of claim 8, wherein the composition is administered on a continuing basis of once or twice a day.

12. The method of claim 9, wherein the composition is administered on a continuing basis of once or twice a day.

13. The method of claim 10, wherein the composition is administered on a continuing basis of once or twice a day.

14. The method of claim 3, wherein the composition is a dry composition formulated as a liquid drink by admixture with a pharmaceutically-acceptable aqueous carrier.

15. The method of claim 14, wherein the composition is administered in single dosages each comprising about 5 to 35 gm of dry PEG dissolved in the aqueous carrier.

16. The method of claim 15, wherein each single dosage further comprises about 10 to 30 gm of dry lactulose dissolved in the aqueous carrier.

17. The method of claim 16, wherein each single dosage comprises about 10 to 20 gm PEG and about 10 to 20 gm lactulose.

18. The method of claim 15, wherein the composition is administered on a continuing basis in at least one single dosage per day.

19. The method of claim 16, wherein the composition is administered on a continuing basis in at least one single dosage per day.

20. The method of claim 17, wherein the composition is administered on a continuing basis in at least one single dosage per day.

21. The method of claim 18, wherein the composition is administered on a continuing basis of once or twice a day.

22. The method of claim 19, wherein the composition is administered on a continuing basis of once or twice a day.

23. The method of claim 20, wherein the composition is administered on a continuing basis of once or twice a day.

24. The method of claim 3, wherein PEG is a solid at room temperature.

* * * * *